(12) United States Patent
Pendharkar et al.

(10) Patent No.: US 8,551,941 B2
(45) Date of Patent: Oct. 8, 2013

(54) PROCESS OF MAKING FLOWABLE HEMOSTATIC COMPOSITIONS AND DEVICES CONTAINING SUCH COMPOSITIONS

(75) Inventors: Sanyog M. Pendharkar, Edison, NJ (US); Anne J. Gorman, Hightstown, NJ (US); Guanghui Zhang, Belle Mead, NJ (US); Ada Rivera, Neshanic Station, NJ (US); Dwayne Lee Looney, Flemington, NJ (US); Thomas Lee Craven, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 6 days.

(21) Appl. No.: 12/902,017

(22) Filed: Oct. 11, 2010

(65) Prior Publication Data

US 2011/0027378 A1 Feb. 3, 2011

Related U.S. Application Data

(62) Division of application No. 11/348,860, filed on Feb. 7, 2006, now Pat. No. 7,833,965.

(51) Int. Cl.
*A61K 38/00* (2006.01)
*A61K 38/48* (2006.01)

(52) U.S. Cl.
USPC .......................... 514/2; 424/94.64

(58) Field of Classification Search
None
See application file for complete search history.

(56) References Cited

U.S. PATENT DOCUMENTS

| | | | |
|---|---|---|---|
| 2,507,244 A | 5/1950 | Correll et al. | |
| 3,743,140 A | 7/1973 | Sauerbrey | |
| 4,655,211 A | 4/1987 | Sakamoto et al. | |
| 4,891,359 A | 1/1990 | Saferstein et al. | |
| 5,143,838 A | 9/1992 | Kraus et al. | |
| 5,595,735 A | 1/1997 | Saferstein et al. | |
| 5,677,284 A | 10/1997 | Li | |
| 5,733,572 A | 3/1998 | Unger et al. | |
| 5,908,054 A | 6/1999 | Safabash et al. | |
| 6,045,570 A | 4/2000 | Epstein et al. | |
| 6,063,061 A | 5/2000 | Wallace et al. | |
| 6,066,325 A | 5/2000 | Wallace et al. | |
| 6,120,751 A | 9/2000 | Unger | |
| 6,432,415 B1 | 8/2002 | Osborne et al. | |
| 6,566,345 B2 | 5/2003 | Miller et al. | |
| 6,605,066 B1 | 8/2003 | Gravagna et al. | |
| 6,869,938 B1 | 3/2005 | Schwartz et al. | |
| 7,109,163 B2 | 9/2006 | Pendharkar et al. | |
| 7,351,561 B2 | 4/2008 | Metzner et al. | |
| 7,718,412 B2 | 5/2010 | Pendharkar et al. | |
| 7,833,965 B2 | 11/2010 | Pendharkar et al. | |
| 2002/0042378 A1 | 4/2002 | Reich et al. | |
| 2002/0114775 A1 | 8/2002 | Pathak | |
| 2002/0193448 A1 | 12/2002 | Wallace et al. | |
| 2003/0028140 A1 | 2/2003 | Greff | |
| 2003/0064109 A1 | 4/2003 | Qian et al. | |
| 2003/0077272 A1 | 4/2003 | Pathak | |
| 2003/0129183 A1 | 7/2003 | Spillert et al. | |
| 2005/0037088 A1 | 2/2005 | Pendharkar et al. | |
| 2006/0127488 A1 | 6/2006 | Pendharkar et al. | |

FOREIGN PATENT DOCUMENTS

| | | |
|---|---|---|
| CA | 2495048 | 1/2005 |
| EP | 0 740 528 B1 | 3/2003 |
| EP | 0 927 053 B1 | 4/2003 |
| EP | 1 559 438 A1 | 8/2005 |
| GB | 1 018 647 | 1/1966 |
| JP | 62-228009 A | 10/1987 |
| JP | 2-218616 | 8/1990 |
| JP | 2000-229882 A | 8/2000 |
| JP | 2001-261574 A | 9/2001 |
| JP | 2002-104996 A | 4/2002 |
| JP | 2003-501215 | 1/2003 |
| WO | 94/23788 | 10/1994 |
| WO | 98/08550 A1 | 3/1998 |
| WO | 00/33894 A1 | 6/2000 |
| WO | 00/76533 A1 | 12/2000 |
| WO | 01/28603 A1 | 4/2001 |
| WO | 01/82937 A1 | 11/2001 |
| WO | 01/97826 A2 | 12/2001 |
| WO | 01/97873 A2 | 12/2001 |
| WO | 02/072128 A1 | 9/2002 |
| WO | 03/007845 A1 | 1/2003 |
| WO | 03/055531 A2 | 7/2003 |
| WO | 2005/016256 A2 | 2/2005 |
| WO | 2005/016257 A2 | 2/2005 |

OTHER PUBLICATIONS

Wikipedia, the free encyclopedia. Hypertext address en.wikipedia.org/wiki/Foaming_agent. (Accessed Apr. 13, 2007).
Wikipedia article (downloaded Nov. 9, 2007): "Foam": website: //en.wikipedia.org/wiki/Foam.
Merriam-Webster Entry (downloaded Nov. 9, 2007): "Foam": website //www.merriam-webster.com/dictionary/foam.

(Continued)

*Primary Examiner* — Anand Desai
(74) *Attorney, Agent, or Firm* — Roberts Mlotkowski Safran & Cole P.C.

(57) ABSTRACT

The present invention includes both sterilized and unsterilized hemostatic compositions that contain a continuous, biocompatible liquid phase having a solid phase of particles of a biocompatible polymer suitable for use in hemostasis and which is substantially insoluble in the liquid phase, and a discontinuous, biocompatible gaseous phase, each of which is substantially homogenously dispersed throughout the continuous liquid phase, methods for making such compositions, medical devices that contain sterilized hemostatic compositions disposed therein and methods of making such devices.

15 Claims, 4 Drawing Sheets

(56) References Cited

OTHER PUBLICATIONS

International Search Report dated Jul. 12, 2005 for corresponding Application No. PCT/US04/23765.
International Search Report dated Dec. 12, 2005 for corresponding Application No. PCT/US04/23799.
Sakurabayashi, "Clinical Evaluation of New Hemostatic Agent for Hemostasis from Biopsy Wounds in the Liver" Gastroenterological Endoscopy, vol. 30(1), (Oct. 1988) pp. 2256.
Supplementary European Search Report dated Aug. 21, 2009 for corresponding application No. EP04779021.
Supplementary European Search Report dated Sep. 8, 2009 for corresponding application No. EP04757245.
www.mathopenref.com/angle.html (accessed Oct. 8, 2008).
U.S. Appl. No. 60/493,116, filed Aug. 7, 2003.
International Application No. PCT/US04/23765 filed Jul. 23, 2004.
International Application No. PCT/US04/23799 filed Jul. 23, 2004.
U.S. Appl. No. 10/768,335, filed Jan. 30, 2004.
U.S. Appl. No. 11/264,584, filed Nov. 1, 2005.
U.S. Appl. No. 10/896,647, filed Jul. 22, 2004.
U.S. Appl. No. 10/896,454, filed Jul. 21, 2004.
U.S. Appl. No. 10/567,388, filed Feb. 7, 2006.
U.S. Appl. No. 11/348,860, filed Feb. 7, 2006.
U.S. Appl. No. 12/750,334, filed Mar. 30, 2010.
U.S. Appl. No. 12/902,017, filed Oct. 11, 2010.

US 8,551,941 B2

PROCESS OF MAKING FLOWABLE HEMOSTATIC COMPOSITIONS AND DEVICES CONTAINING SUCH COMPOSITIONS

CROSS REFERENCE TO RELATED APPLICATIONS

This application is a Divisional of U.S. Ser. No. 11/348,860 filed Feb. 7, 2006, which is a Continuation of U.S. Ser. No. 10/768,335 filed Jan. 30, 2004 and International Application PCT/US2004/023779, filed 23 Jul. 2004, which claims priority from U.S. Provisional Ser. No. 60/493,116 filed Aug. 7, 2003.

FIELD OF THE INVENTION

The present invention relates to methods of making flowable hemostatic compositions and devices containing such compositions.

BACKGROUND OF THE INVENTION

Gelatin-based hemostats, both in solid sponge or powder form, are commercially available and are used in surgical procedures. Gelatin powder, when mixed with fluid, can form a paste or slurry that is useful as a flowable, extrudable and injectable hemostat for diffuse bleeding, particularly from uneven surfaces or hard to reach areas. The conventional slurry is prepared at the point of use by mechanical agitation and mixing of the powder and liquid to provide uniformity of the composition. The paste then is placed into a delivery means or applicator, e.g. a syringe, and applied to the wound.

The main disadvantage of this approach is the need to mix the powder with the liquid, knead it into a paste and back-fill it into the delivery device of choice, all at the time of need and at the point of use. The manipulations are time consuming and potentially may compromise the sterility of the delivered product depending on the environment of use. Thus, a need exists for a sterile, flowable, hemostatic composition that is ready to use at the point of use or can be prepared with minimal manipulation and without risk of compromising the sterility of the product.

It would be desirable if a hemostatic device, e.g. a delivery means such as a syringe or other applicator, would be pre-filled with a hemostatic composition and available to the surgeon at the point of use without need for further manipulation or with minimal manipulation or preparation. The hemostatic composition pre-filled in the device or applicator should be sterile and flowable and should require minimum preparation time and minimal force when extruded or injected through the delivery means at the point of use. It also would be desirable to devise processes for making such compositions that are commercially viable, maintain an acceptable environment in the work place and provide a pre-filled device comprising a hemostatic composition that is flowable and physically stable. The present invention provides such processes.

SUMMARY OF THE INVENTION

The present invention is directed to processes of making flowable hemostatic compositions and devices that are suitable for use in applying such flowable hemostatic compositions and that comprise the flowable hemostatic composition disposed therein. In a process for making the flowable hemostatic composition, a first volume of a biocompatible liquid is introduced into a mixing vessel equipped with a means for mixing the liquid. A second volume of a biocompatible gas is introduced into the volume of liquid while the means for mixing is operating under conditions effective to mix the liquid and the gas together to form a foam. The foam comprises a discontinuous gas phase comprising the gas dispersed throughout a continuous liquid phase comprising the liquid. An amount of solid particles of a biocompatible polymer suitable for use in hemostasis and which is substantially insoluble in the liquid is introduced into the foam and the foam and the solid particles are mixed together under conditions effective to form a substantially homogenous composition comprising the discontinuous gas phase and the solid particles substantially homogenously dispersed throughout the continuous liquid phase. The ratio of the volume of liquid, volume of gas and amount of solid particles is effective to provide the hemostatic composition with hemostatic properties, thus forming the flowable hemostatic composition. The flowable hemostatic composition so formed is then transferred into a device suitable for applying the flowable hemostatic composition to a site of a body requiring hemostasis under conditions effective to maintain the substantially homogeneous dispersion of the gas phase and the solid particles throughout the liquid phase. The device comprising the flowable hemostatic composition disposed therein is subjected, or exposed, to conditions effective to provide a sterile device comprising a sterile, flowable hemostatic composition. Compositions and devices made by the processes of the present invention may be prepared well in advance of the time of use and need not be prepared at the point of use, yet they maintain physical properties effective to provide flowability, extrudability or injectability at the point and time of use.

DETAILED DESCRIPTION OF THE INVENTION

Figure 1:
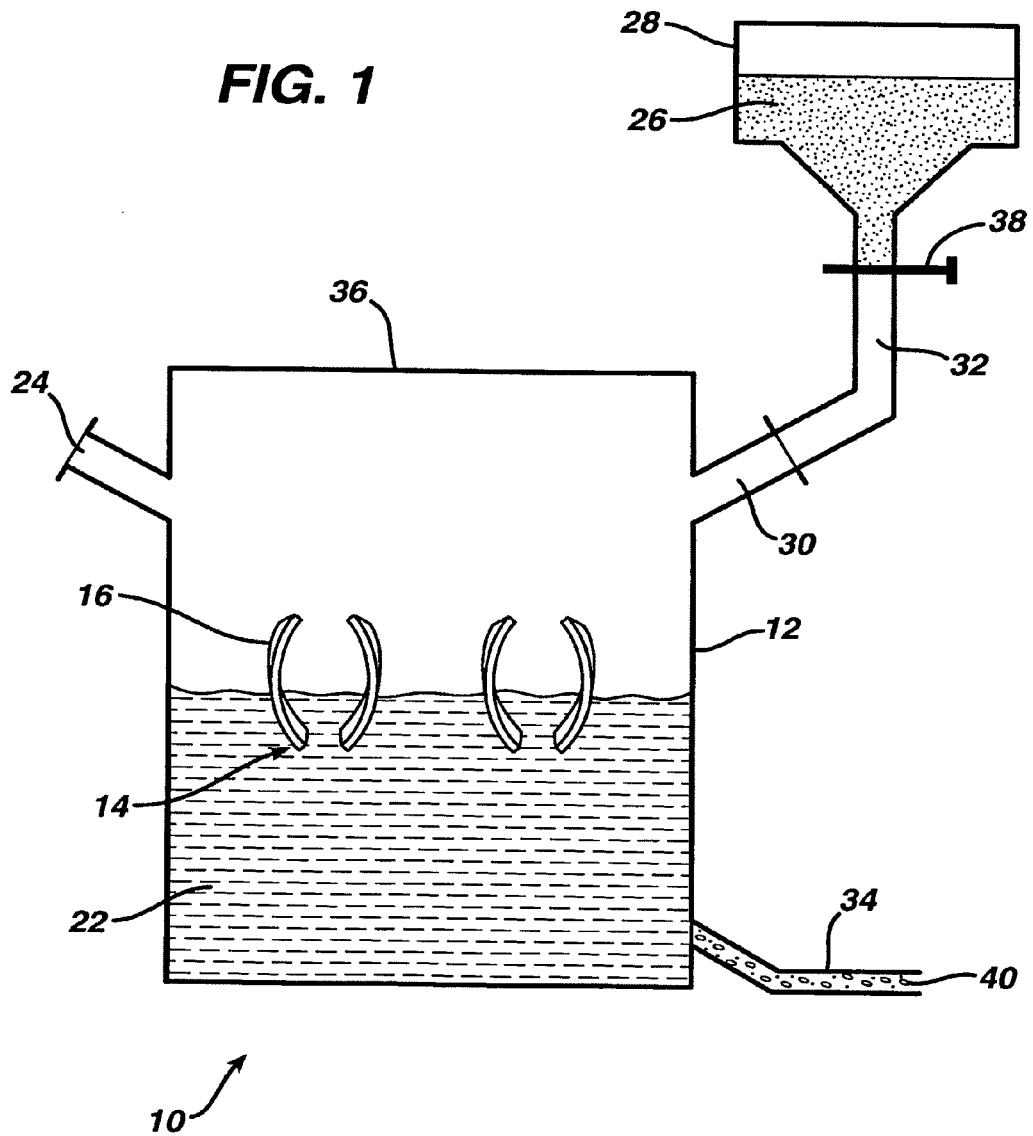
FIG. 1 is a schematic cross-sectional side view of a mixing apparatus used in processes of the present invention.

Both sterilized and unsterilized compositions made by processes of the present invention contain solid, porous or non-porous particles of a biocompatible polymer suitable for use in hemostasis, a biocompatible liquid and a biocompatible gas as its three necessary components. The particles, liquid and gas are combined and mixed under conditions effective to provide a substantially homogeneous hemostatic composition comprising a continuous liquid phase comprising the liquid, and the solid polymer particles and a discontinuous gas phase comprising the gas homogenously dispersed through the continuous liquid phase. The amount and average diameter of particles contained in the composition and the relative amount of the solid, liquid and gaseous phases is effective to provide the composition with hemostatic and physical properties, as described herein below.

The hemostatic composition so formed is a hemostatic paste, or slurry, that exhibits improved properties of flowability, extrudability and/or injectability when compared to flowable hemostatic compositions of similar liquid/particle composition but that do not contain a gaseous phase dispersed therethrough. Compositions made by the processes of the present invention may be prepared, filled into a medical device, such as a syringe or other known applicators used to dispense flowable hemostatic compositions, and sterilized by ionizing irradiation, well in advance of the time of their intended use. The compositions further may include additives to facilitate the preparation of the composition, enhance physical and mechanical properties, enhance the hemostatic properties of the composition, or provide antimicrobial properties.

As used herein, "continuous" and "discontinuous" are used in the ordinary meaning of those words in the context of standard nomenclature used to define and describe dispersions. For example, when combined and mixed with the continuous liquid phase, the volume of biocompatible gas added to the liquid phase is disrupted by mixing so as to form the discontinuous, i.e. dispersed, gaseous phase comprising pockets or isolated bodies of gas.

As used herein, "substantially homogenous" denotes that physical state of the compositions or pastes where the solid and/or gaseous phases are uniformly dispersed throughout the continuous liquid phase such that the ratio of solid:gas:liquid and the density of any portion or cross-section of the composition or paste are substantially the same.

As used herein, "foam" denotes that state where the discontinuous gas phase has been dispersed in the continuous liquid phase. The gas phase in the foam need not be substantially homogenously dispersed through the foam.

As used herein, "density" is used in the ordinary meaning of the word in the context of standard nomenclature used to define and describe the mass of the mixture of the solids and the added liquid per unit volume of the foamed paste.

As used herein, "sterile" means substantially free of living germs and/or microorganisms and as further recognized and described by governmental standards pertaining to compositions and medical devices described and claimed herein. As used herein, "hemostatic", or "hemostatic properties", means the ability to stop or minimize bleeding, as one skilled in the art of hemostasis would understand those terms to mean, as further exemplified in the examples of the specification.

As used herein, "peak expression force" is the peak force value required to extrude compositions from a pre-filled luer syringe fitted with a 14 gauge angiocatheter tip, as described in the examples of the specification.

A variety of biocompatible natural, semi-synthetic or synthetic polymers may be used to prepare the solid particles used in compositions of the present invention. The polymer selected must be substantially insoluble in the liquid chosen for the particular composition. Preferably, water-insoluble biodegradable polymers that provide mechanical, chemical and/or biological hemostatic activity are used.
Polymers that may be used include, without limitation, proteins and polysaccharides. Polysaccharides that may be used include oxidized cellulose, chitosan, chitin, alginate, oxidized alginate and oxidized starch. The biocompatible polymer used to prepare the particles preferably is a cross-linked or denatured protein, such as gelatin, collagen, fibrinogen or fibronectin. A preferred gelatin powder is a partially cross-linked gelatin powder prepared by milling gelatin sponge into particles having an average diameter of from about 40 microns to about 1200 microns, or from about 100 microns to about 1,000 microns, as determined by laser diffraction.

Compositions made by processes of the present invention comprise a continuous liquid phase in which the solid particles and gaseous phase are substantially homogenously dispersed. Depending upon the particular medical device and use thereof, the liquid may be aqueous or non-aqueous. In certain embodiments, the liquid phase is aqueous. Aqueous liquids may include, without limitation, biocompatible aqueous solutions, such as calcium chloride and saline. More preferably, the liquid phase comprises saline. The liquid phase and solid particulate phase are present in relative amounts effective to provide a paste, or slurry, suitable for use in providing hemostasis. Excessive dilution of the solid particulate phase, although beneficial to further reduce the peak expression force, will detrimentally affect the hemostatic properties of the material and therefore is not desired. The weight ratio of solid particles to liquid generally is from about 1:2 to about 1:12. In certain embodiments the weight ratio of solid gelatin particles to saline is from about 1:3 to about 1:6. In yet other embodiments the weight ratio of solid gelatin particles to saline is about 1:5.

Any biocompatible gas may be used to prepare compositions of the present invention, including, but not limited to, air, carbon dioxide, nitrogen, xenon or argon. Preferably an inert gas such as argon or nitrogen is used. Air, nitrogen and argon are sensitive to ultrasound and may provide a means to locate the composition once injected in the body. Similarly, as xenon is radio-opaque, using xenon also may provide a means to locate the composition once placed in the body. In addition, as carbon dioxide lowers pH, selection of carbon dioxide may enhance antimicrobial properties of the compositions. The gas is combined and mixed with the continuous liquid phase until it is dispersed throughout the liquid phase so as to form a discontinuous gaseous phase dispersed in the continuous liquid phase so as to form a foam. Upon formation of the composition by dispersion of the particles in the foam, the dispersion of the gas phase in the composition provides the composition with improved physical properties relating to flowability, extrudability and injectability, as described herein. Such improved properties are characterized by way of physical measurements of the compositions, including density and peak expression force, both prior to and after irradiation of the compositions during sterilization.

The relative concentration of the three major components of the compositions of the present invention and the substantially homogenous nature of such compositions are key in providing both hemostatic and physical properties to the compositions. The solid particles, liquid phase and gaseous phase generally will be present in compositions made by processes of the present invention at a ratio of from about 1:2:1 to about 1:12:13, based on weight:volume:volume (g:ml:ml). In other embodiments the ratio will be from about 1:4:1 to about 1:8:9. In yet other embodiments the ratio will be about 1:5:3. The density of compositions of the present invention will be from about 0.9 g/ml to about 0.3 g/ml, or in certain embodiments from about 0.8 g/ml to about 0.6 g/ml.

Certain compositions made by the processes of the present invention described herein are sterile, in that they have been irradiated with a level of, e.g. ionizing irradiation. Such irradiation may include e-beam or gamma irradiation. The level of irradiation and conditions of sterilization, including the time that the compositions are irradiated, are those that provide sterile compositions, as defined herein. Once having the benefit of this disclosure, one skilled in the art will be able to readily determine the level of irradiation necessary to provide sterile compositions.

The hemostatic compositions may further comprise effective amounts of one or more additives or compounds including, but not limited to, radio opaque agent, antimicrobial agents, foaming agents, foam stabilizers, surfactants, antioxidants, humectants, wetting agents, lubricants, thickeners, diluents, irradiation stabilizers, e.g. radical scavengers, plasticizers, and stabilizers. For example, glycerol may be added to enhance the extrudability or injectability of the composition. Glycerol may be present in the compositions up to about 20% by weight, or from about 1% to about 10%, or from about 1% to about 5%, based on the weight of the liquid phase. In addition, quaternary amines may be used to provide enhanced properties to the compositions. For example, benzalkonium chloride, Polybrene or Onamer M may be used at levels up to about 1 percent by weight, based on the weight of the liquid phase. In certain embodiments benzalkonium chloride is used at levels of from about 0.001% to about 0.01%, or from about 0.002 to about 0.006% by weight, based on the weight of the liquid phase. It is believed that the quaternary amines may serve multiple functions, acting as an antimicrobial agent, a foaming agent, a radical scavenger and/or as a heparin neutralizer.

Such hemostatic compositions may further comprise effective amounts of heparin neutralizers, procoagulants or hemostatic agents, such as thrombin, fibrinogen, fibrin, Factor Xa, or Factor VIIa. By "effective amount", it is meant that amount necessary to provide to the compositions those properties for which the additive is being added. The maximum amount that may be added is limited so as not to cause detrimental biological affects.

Compositions made by processes of the present invention are particularly advantageous for use in hemostatic compositions where additives that are sensitive to irradiation, are utilized. For example, thrombin, in an aqueous solution, has been found to lose all procoagulant activity when exposed to sterilization irradiation. In contrast, thrombin retained approximately 40% of its original enzymatic activity and all of its hemostatic activity after sterilization when formulated in compositions according to this invention, as shown in Example 9. While bovine thrombin is exemplified herein, human-derived thrombin such as described in U.S. Pat. No. 5,143,838, the content of which is hereby incorporated by reference herein in its entirety, also may be used in compositions of the present invention.

Medical devices in which the hemostatic compositions of the present invention may be utilized include any device currently being used to apply a flowable or injectable hemostatic paste or slurry to a site, or wound, requiring hemostasis. The site requiring hemostasis may be the result of an injury or a surgical procedure. Examples of devices or applicators include syringes such as Becton Dickinson or Monoject luer syringes. Other devices are disclosed in detail in U.S. Pat. No. 6,045,570, the contents of which are incorporated by reference in their entirety.

In processes of the present invention, the liquid is added to the mixer. The gas then is incorporated into the liquid with mixing under conditions effective to form a foam comprising a discontinuous gas phase of the gas dispersed through a continuous liquid phase of the liquid. In certain embodiments the gas and liquid may be mixed for from about 3 to about 30 minutes. The solid polymer particles are then incorporated into the foam and mixed so as to substantially homogenously disperse the solid particles throughout the foam. In certain embodiments the foam and particles may be mixed for from about 15 to about 30 minutes, although mixing for more than 30 minutes is acceptable. In such embodiments a mixer, e.g. a double planetary mixer, may be utilized.

The liquid may include effective amounts of additives dissolved therein prior to addition of particles or the gas to the solution. For example, a saline solution containing glycerol and benzalkonium chloride may be prepared and then added to the mixer. A source of gas is provided to the mixer whereby a first portion of the gas may be added to the liquid solution. The mixture of gas and liquid is mixed to disperse the gas in the liquid phase, thus forming a foam. The solid particles and any additional portion of gas then are added to the mixer over time with continuous mixing until all ingredients have been added. The mixing is continued until such time as a substantially homogenous composition is formed containing the solid particles and discontinuous gaseous phase uniformly dispersed throughout the continuous liquid phase. The density of the mixture of liquid, gas and solid particles may be monitored to determined at what point the composition is substantially homogeneous so as to provide the composition with desired physical and hemostatic properties.

The flowable hemostatic compositions so formed are then transferred into a device suitable for applying the flowable compositions to a site of the body requiring hemostasis. The filled device and composition contained therein then are sterilized to provide a sterile, ready-to-use system that avoids issues of the current state of the art with regards to on-site preparation and handling just prior to use.

While preparation of compositions and devices noted above may be readily achieved on a small scale, such as a laboratory setting, the preparation of such compositions and devices on a scale suitable for commercial use presents additional issues.

In a commercial manufacturing setting, certain issues not readily apparent in the small scale preparation of compositions and devices must be addressed, including the general environment of the workplace, potential increased bioburden of the solid particles due to exposure to the atmosphere, and maintaining the physical structure and properties of the compositions during transfer to the applicator devices and sterilization. For example, when a large quantity of fine particles in the form of a powder are added to a mixing vessel, the fine particle size of the particles in the powder may cause excessive dusting in the workplace, which may create environmental concerns, including issues related to personnel safety and general maintenance of the workplace, as well as the qualification grade of the facility. Additionally, gelatin based materials, for example, when exposed to the environment for a prolonged period of time, may be subject to infestation by microorganisms. The increased bioburden of the powder may lead to degradation of the gelatin during processing and may be detrimental to the sterility and biocompatibility of the product.

In order to minimize the environmental issues that may be caused by excessive dusting, one solution may be to compact or condense the particles into a physical body, such as pellets, granules or any other appropriate shape prior to the mixing. The body of particles may, but need not, comprise a plurality of packed particles comprising interstitial pores having a pore volume and a median pore diameter effective to provide improved absorption of an aqueous media into the interstitial pores when placed in contact therewith, compared to a plurality of unpacked particles.

Alternately, the solid particles may be added to the mixing vessel containing the foam through a structure or conduit that is closed or sealed so as to avoid exposure of the powder particles to the atmosphere during addition. Adding the particles via such a structure minimizes dusting caused by the addition of fine particles, as well as reduces the opportunity for the growth of microorganisms on the residual particles previously trapped on the inner wall of the mixing vessel prior to incorporation.

In addition to environmental issues as discussed above, transfer of the flowable hemostatic compositions from the mixing vessel to the medical devices may lead to the breakdown or deformation of the physical structure of the composition, i.e. disruption of the dispersion of the solid particles and gas phase throughout the liquid phase. If one were to attempt to transfer the substantially homogenous hemostatic composition from the mixing vessel to the applicator device by relatively high pressure, it may be difficult to maintain the structure of the hemostatic composition due to compression forces that may arise due to the relatively high pressure required to move the paste in such instances. Such compression could lead to separation of the gaseous phase from the liquid phase. Such a loss of the gaseous phase is detrimental to the mechanical properties of the composition, e.g. flowability and ease of mixing, both during and after the irradiation process.

The processes of the present invention minimize such detrimental effects by transferring the composition throughout the process under conditions that avoid the creation or presence of appreciable pressures that may lead to compression forces. Preferably, the composition is transferred from the mixing vessel into the applicator device in the substantial absence of such compression forces and under minimal pressure conditions, meaning those conditions that provide for efficient transfer of the composition without detrimentally affecting the structure of the composition.

In order to maintain minimal pressure conditions, certain embodiments of processes of the present invention utilize an auger screw to transfer the hemostatic composition into the applicator device. In certain embodiments exemplified herein, the auger screw is used in a vertical orientation to take advantage of gravitational forces for filling the devices, although it is contemplated that transfer of the composition from the mixing vessel to a filling apparatus could be conducted with a horizontal screw orientation. The auger screw provides for local movement of the compositions through the process versus bulk transfer. In this way, large forces applied to the bulk of the composition that may lead to compression on the whole of the body of material may be avoided in lieu of localized forces within the body of material.

As the compositions prepared according to the present invention comprise gaseous, liquid and solid phases, as described above, maintaining the structure of the composition will depend in part on the design of the auger screw. To maintain the structure and ratios of liquid:gas:solid particles of the compositions within acceptable parameters, and thus the density of the extruded hemostatic paste within an acceptable density range, considerations for an auger design include the width, number and pitch of the flights on the auger screw, the angle of the flight to the auger screw rod, the design and finish of the auger bowl, the diameter and angle of the agitator blade and on the overall scale of the apparatus.

Once transferred into the holding vessel of the filling apparatus, maintaining conditions effective to maintain the structure of the compositions during filling will depend on a number of aspects. One consideration is the amount of work that may be imparted to the compositions either by the auger screw or by gravitational forces exerted on the bulk of the composition. The resident time of the compositions within the filling apparatus is related to each of these considerations. The longer the composition is held within the filling apparatus, the longer it is subjected to repetitive, pulsing forces created by the auger screw during filling and the longer it has to have the weight of the body of the composition act to compress the composition itself, each of which may lead to separation of the gas phase from the liquid phase. In addition, the configuration and finish of the auger bowl must be considered. Surface finishes that minimize friction between the material and the sides of the auger bowl will minimize any detrimental effects that may be caused by friction.

It was found that the resident time of the compositions in the filling apparatus, the overall work imparted to the compositions and the rate of transferring the compositions into the applicator device may be optimized such that the adverse effects, as stated above, may be minimized. With respect to specific embodiments exemplified herein, it was found that the rate of transfer of the composition from the holding vessel of the apparatus to the devices advantageously is at least about 12 ml/minute, or at least about 36 ml/minute, or even about 72 ml/minute, and even more than about 100 ml/minute. It will be understood by those skilled in the art that the actual rate at which the composition is transferred in order to optimize resident time work imparted to the composition, however, will depend upon the particular design and size of the filling apparatus, as well as the particular composition being filled.

As shown in FIG. 1, mixing apparatus 10 includes mixing vessel 12, equipped with mixing means 14. Mixing means 14 comprises multiple helical blades 16 that rotate on their own axes, while orbiting mixing vessel 12 on a common axis. Helical blades 16 continuously advance around the periphery of mixing vessel 12, removing material from internal mixing vessel wall 18 and transporting to the interior of mixing vessel 12, thus allowing the entire batch of materials to be mixed thoroughly. Mixing vessel 12 is fit with mixing vessel cover 36 so as to provide a closed system. Mixing cover 36 includes addition ports 24, 30 and 34 for addition of liquid 22, gas 40 and solid particles 26 into mixing vessel 12. Hopper 28 containing solid particles 26 is in a closed relationship with mixing vessel cover 36 via conduit 32 including powder flow regulating valve 38 to minimize exposure of solid particles 26 from the atmosphere.

In one embodiment of the process, liquid 22 is added to mixing vessel 12 via port 24. Mixing means 14 is engaged at a rate of from about 60 to about 80 Hz to facilitate mixing of gas 40 and liquid 22 when the two are placed together. Gas 40 is introduced into liquid 22 in mixing vessel 12 via port 34. Liquid 22 and gas 40 are mixed at a rate and for a time effective to provide a foam as described herein above. Solid particles 26 are then introduced into the foam via conduit 32. The foam and solid particles 26 are then mixed at a rate and for a time effective to substantially homogenously disperse particles 26 throughout the foam. Once prepared, the flowable hemostatic composition is transferred to a holding vessel of a filling apparatus shown in FIG. 2 for subsequent filling into an applicator device. The transfer of the hemostatic composition to the holding vessel may be conducted manually, e.g., by using a sterile scoop, as described herein, or by any automated means.

Figure 2:
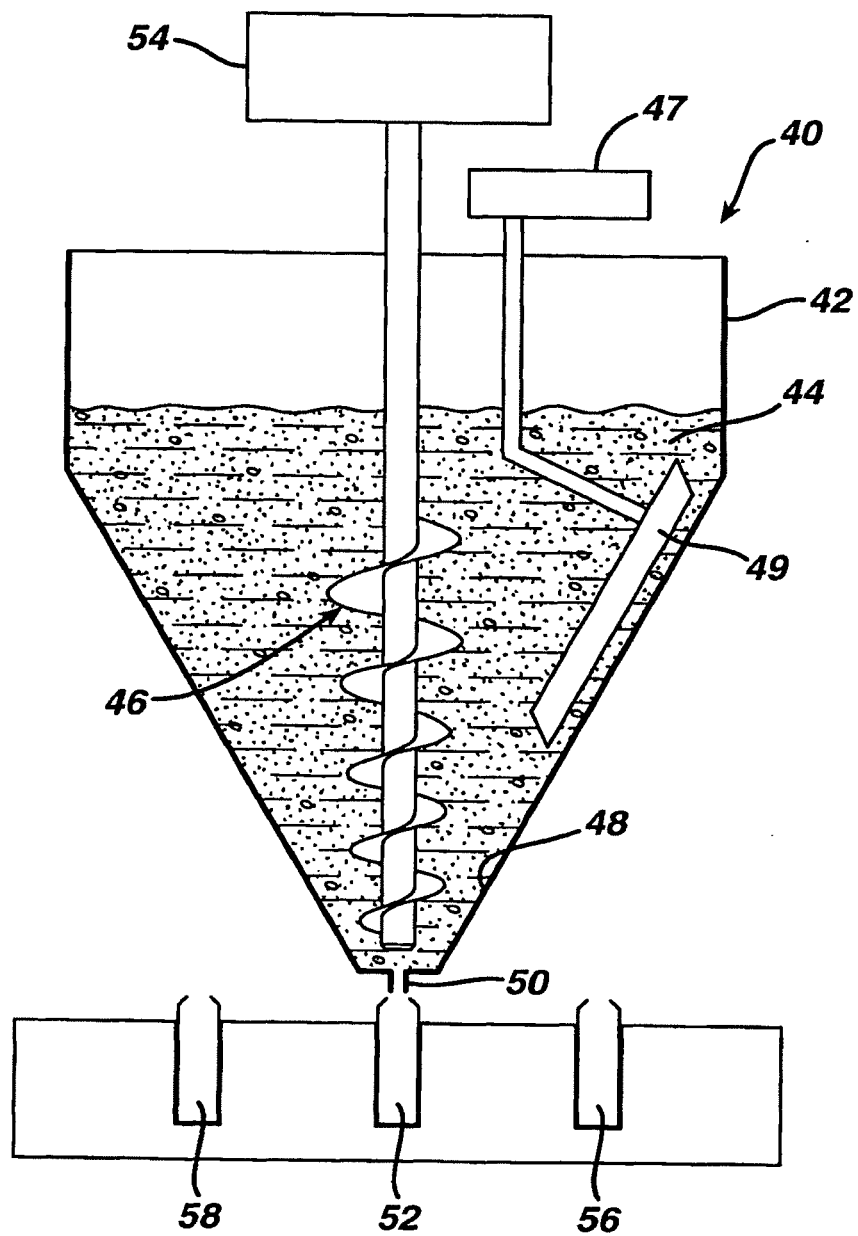
FIG. 2 is a schematic cross-sectional side view of a filling apparatus used in processes of the present invention.

As shown in FIG. 2, filling apparatus 40 includes holding vessel 42 for holding flowable hemostatic composition 44 and auger screw 46 disposed within holding vessel 42 and auger funnel 48 and in cooperation with motor 54 and agitator blade 49 in cooperation with motor 47. Auger screw 46 transports flowable hemostatic composition 44 from holding vessel 42 and through auger funnel 48 in a downward spiral fashion. Agitator blade 49 serves to prevent material from building on the walls of the holding vessel while also maintaining the homogenous structure of the composition during filling. Flowable hemostatic composition 44 then is transferred into applicator device 52 via exit port 50. As composition 44 is filled into devices 52, 56, 58, auger screw 46 is in operation to affect transfer. After device 50 is filled, operation of auger screw 46 is disrupted and the stream of the composition separated to provide for subsequent filling of additional devices 56 and 58. The repeated disruption of flow creates a pulsating force upon composition 44 within holding vessel 42. This repeated mechanical manipulation of the composition may detrimentally affect the composition properties. Thus, as discussed above, the design of auger screw 46 and the rate of filling devices 52, 56 and 58 are optimized to minimize negative effects.

Figure 3:
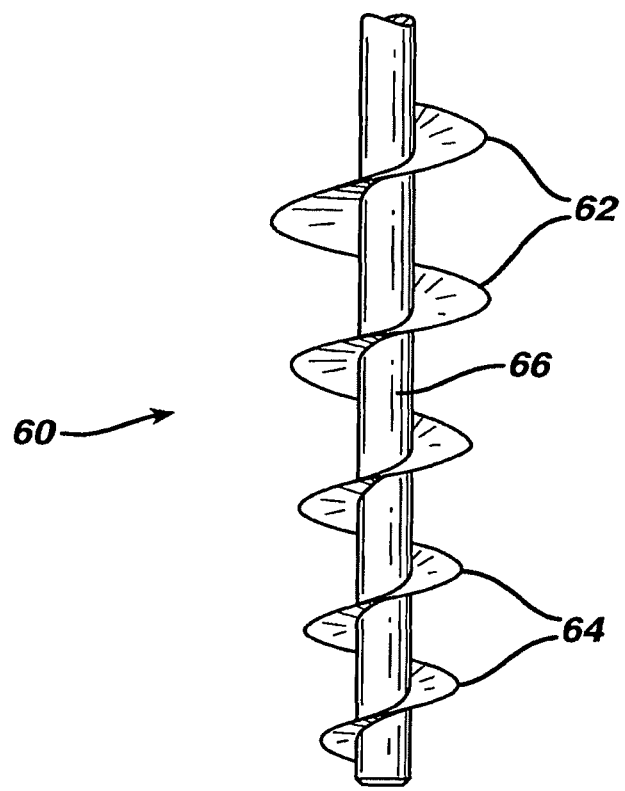
FIG. 3 is a side perspective view of an auger screw of the type used in processes of the present invention.

An auger screw of the type that may be used in processes of the present invention is shown in FIG. 3. As shown, screw 60 comprises multiple flights 62, 64 attached to auger screw rod 66. As shown, flight 62 has a greater diameter than flight 64. In embodiments of the present invention, the number, diameter, angle and distance between fights may be designed to accommodate particular apparatus being used or the composition itself. One skilled in the art will be able to readily ascertain other screw designs that may be employed in processes of the present invention once having the benefit of this disclosure.

Figure 4A:
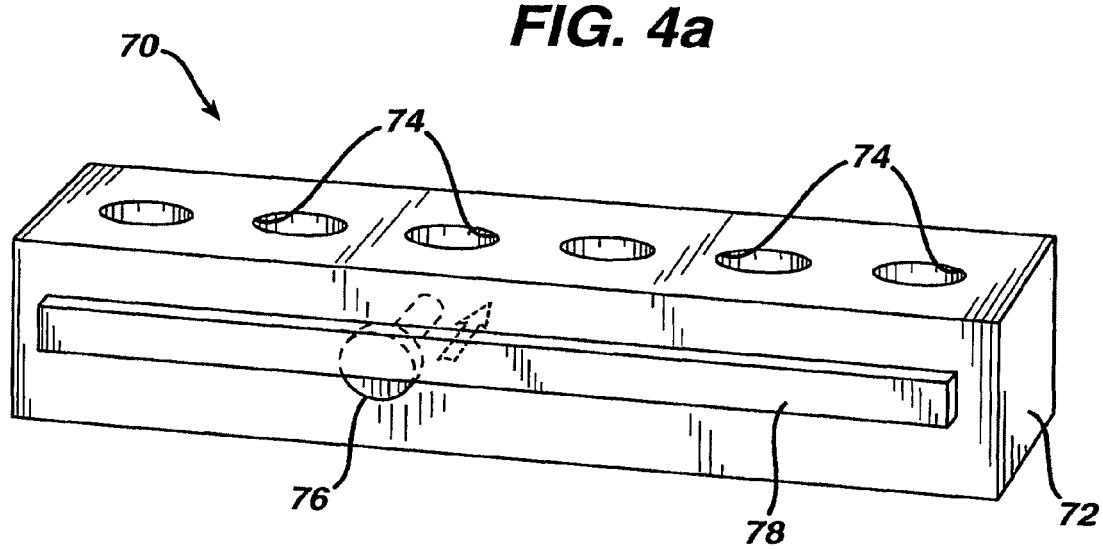
FIG. 4a is a side elevation view of an apparatus used in processes of the present invention.
Figure 4B:
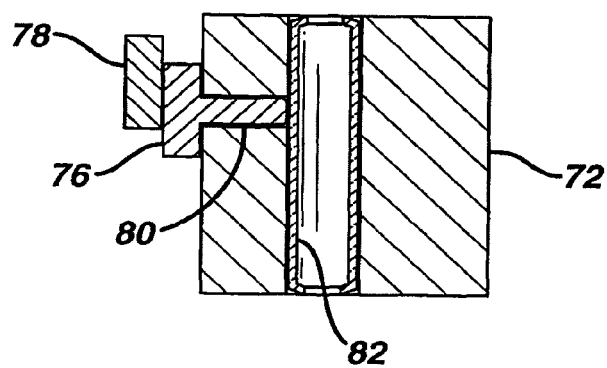
FIG. 4b is a cross-sectional side view of an apparatus used in processes of the present invention.

The auger screw transfers the composition from the holding vessel into the applicator devices. FIGS. 4a and 4b depict a typical fixture that may be used to hold applicator devices such a syringes during the filling process. Fixture 70, i.e. the syringe loading station, is equipped with syringe holder 72 having multiple syringe receptacles 74, and means for securing the syringes to fixture 70 that includes clamping screw 76, clamping rod 78, and syringe impingement pin 80. Syringe 82 is placed within syringe receptacle 74. Each syringe is back-filled with the same volume of paste in a sequential manner using the apparatus described above. The back-filling operation involves dispensing the composition into syringe 82 from the back end of syringe 82. Syringe 82 is held in place by clamping screw 76. Upon completion of filling, Syringe impingement pin 80 contacts the external of syringe 82, thus creating pressure on syringe 82 that results in the separation of the stream of composition between syringe 82 and the port of the filling apparatus. Fixture 70 then indexes such that next syringe 82 is moved to be in a filling position. Once filled, the syringe plunger is inserted into the back end of the filled syringe and advanced to its appropriate position, followed by capping of syringe 82.

Alternately, the basic design of the means for transfer of the material into the device, including securing the syringe, use of the impingement pin to affect separation of the material stream, indexing the multiple syringes in a vertical motion followed by horizontal motion may be automated. For example a circular fixture comprising multiple receptacles may index in a circular manner to provide filling of the device.

One skilled in the art may envision other means for manufacturing such compositions and filling them into devices. For example, a pump technique can be used whereby powder can be added to a re-circulating loop of foaming solution. The foaming solution may be pumped utilizing a low-shearing pump pump and the powder can be added until the desired properties have been achieved. Once the desired ratio of liquid to solid is reached, the gas will be introduced into the re-circulating paste. A chamber can be included to allow for the expansion of the paste. When the chamber is full, such that the desired density is reached, the foamed paste can be continuously filled into syringes.

Given that the density of the flowable hemostatic composition is an indicator of acceptable mechanical and hemostatic properties of the compositions, the density of the flowable hemostatic composition is measured upon completion of mixing to ensure acceptable properties. One method of assessing the density used and described herein includes suspending the hemostatic composition in a series of organic solvents of known densities or measuring the weight of a known volume of the composition, although other methods of measuring density could be utilized. In monitoring the density of compositions in processes of the present invention, the density of the flowable hemostatic composition is assessed by using inert organic liquids with known densities. The liquids are selected such that any possible interactions with the compositions will have no impact on the measurements. The choice of the solvent density coincides with the predetermined acceptable density range of the hemostatic composition. The composition is placed in a series of solvents of varying densities and the density of the composition determined based on whether it sinks or floats in the solvent.

The hemostatic compositions prepared as above are transferred into a medical device as described above and the device containing the hemostatic composition is sterilized, preferably by ionizing radiation. More preferably, sterilization is by gamma irradiation as exemplified herein.

While the following examples demonstrate certain embodiments of the invention, they are not to be interpreted as limiting the scope of the invention, but rather as contributing to a complete description of the invention.

EXAMPLES

Samples prepared in the examples below were tested for peak expression force as determined using a Chatillon TCD 200, using a 50-lb load cell [DFG 550] at a speed of 2 inches/minute. An in-dwelling catheter sheath (size 12-14 gauge) was attached to the sample syringe to be tested. The syringe then was inserted into a holding apparatus, which then was loaded onto the test instrument. The peak expression force was noted.

Example 1

A total of ten samples were prepared as follows. One gram of dry Surgifoam® powder was placed in a plastic container and mixed with 4 ml of saline. The container was capped and the contents were shaken until a substantially homogenous paste of uniform consistency was obtained. The paste was formed into a cylindrical shape and placed into a 10 cc BD polypropylene disposable luer syringe. The syringes were then capped and five of the filled syringes were sterilized by gamma irradiation at a dose of 25 kGy. The Peak Expression Force was determined and presented in Table 1. Unsterilized samples are designated as 1a and sterilized samples are designated as 1b.

At total of 10 samples were prepared as follows. 1 gm of dry Surgifoam® powder was placed in a plastic container and mixed with 4 ml of saline. The container was capped and the contents were shaken until a substantially homogenous paste of uniform consistency was obtained. The paste was formed into a cylindrical shape and placed into a 10 cc BD polypropylene disposable luer syringe. A second 10 cc BD luer syringe containing 3 ml of nitrogen then was connected to the syringe containing the paste such that the paste could be passed from syringe to syringe. The paste and gas were extruded back and forth between the syringes to thoroughly mix and disperse the gas throughout the paste until a substantially homogeneous foam-like composition of uniform consistency was obtained. The syringes were then capped and five of the filled syringes were sterilized by irradiation at a dose of 25 kGy. The Peak Expression Force was determined and presented in Table 1. Unsterilized samples are designated as 1a' and sterilized samples are designated as 1b'.

Example 2

A total of ten samples were prepared as follows. A saline solution containing 0.005% by weight of benzalkonium chloride and 5% weight of glycerol was prepared. This solution was used to prepare homogenous gelatin-powder pastes as described in Example 1. The paste was formed into a cylindrical shape and placed into a 10 cc BD polypropylene disposable luer syringe. The syringes were then capped and five of the filled syringes were sterilized by irradiation at a dose of 25 kGy. The Peak Expression Force was determined and presented in Table 1. Unsterilized samples are designated as 2a and sterilized samples are designated as 2b.

A total of ten samples were prepared as follows. A saline solution containing 0.005% by weight of benzalkonium chloride and 5% by weight of glycerol was prepared. This solution was used to prepare homogenous gelatin-powder pastes as described in Example 1. A second 10 cc BD luer syringe containing 3 ml of nitrogen then was connected to the syringe containing the paste such that the paste could be passed from syringe to syringe. The paste and gas were extruded back and forth between the syringes to thoroughly mix and disperse the gas throughout the paste until a homogeneous foam-like composition of uniform consistency was obtained. The syringes were then capped and five of the filled syringes were sterilized by irradiation at a dose of 25 kGy. The Peak Expression force was determined and presented in Table 1. Unsterilized samples are designated as sample 2a' and sterilized samples are designated as 2b'.

TABLE 1

| Samples | Peak Expression Force pounds (n = 5) |
|---|---|
| Samples 1a | 21.8 |
| Samples 1b | 26.4 |
| Samples 1'a | 12.0 |
| Samples 1'b | 21.0 |
| Samples 2a | 17.2 |
| Samples 2b | 22.4 |
| Samples 2'a | 11.8 |
| Samples 2'b | 16.8 |

As the data in Table 1 indicates, the inclusion of the gaseous phase homogenously dispersed throughout the paste significantly reduces the peak expression force of the composition prior to sterilization compared to pastes that do not include the homogenously dispersed gaseous phase or other additives. Consequently, the sterilized composition including the homogenously dispersed gaseous phase exhibits an expression force significantly less than that of a sterilized paste that does not include the homogenously dispersed gaseous phase. In fact, the sterilized composition including the gas phase approximates the expression force of the pre-sterilized paste containing no gaseous phase or additives. Thus, a fully sterilized composition may be provided with flowability and/or injectability, as evidenced by peak expression force, equal to or better than that of an unsterilized paste containing no gaseous phase or additives, which is beneficial to health care providers at the point of use. The use of additives, e.g. benzalkonium chloride and glycerol, may be used to further enhance the properties of the compositions of the present invention upon sterilization.

Example 3

25 grams of Surgifoam® gelatin powder were mixed with 125 ml of normal saline containing 0.005% benzalkonium chloride and 5% glycerol, based on weight of saline, until a uniform paste was formed. The resulting paste was loaded into a ½ pint Donvier mixer fitted with a mixing paddle. A tube connected to a nitrogen source was fitted through the lid of the mixer and the system "closed" to the environment by wrapping in a film. The system was purged with nitrogen for 20 minutes. The paste was then mixed to homogenously incorporate the nitrogen by rotating the paddle rapidly by hand. Mixing was terminated when the composition filled the available volume, indicating homogeneous distribution of the gas phase. The composition was loaded into a 60 cc syringe and subsequently dispensed into 10 cc BD luer syringes via a two-way luer connector. The density of the composition was approximately 0.7-0.75 grams/ml. The syringes were then capped and some of the filled syringes were sterilized by irradiation at a dose of 25 kGy.

Example 4

2.5 liters of normal saline containing 0.005% benzalkonium chloride and 5% glycerol dissolved therein, based on the weight of saline, were added to a 2-gallon double planetary Ross mixer and mixed at maximum speed with a first portion of nitrogen for 5 minutes to form a foamed liquid. 500 grams of gelatin powder and the balance of nitrogen were added to the foamed liquid over a 12-minute time period with continuous mixing. The composition was mixed for a further 10 minutes after all of the powder and gas was added. The density of the resulting composition was 0.6 grams/ml. The composition was dispensed into 12 cc Monoject syringes.

Example 5

One-gram samples of Surgifoam® gelatin powder each were mixed with 5 ml of a saline solution containing 0.005% benzalkonium chloride and 5% glycerol to form uniform pastes. The resulting paste was back-loaded into 10 cc BD luer syringes. All air was extruded from the syringes, leaving the paste packed in the syringe. The first set of syringes was irradiated with no gas incorporated therein and designated as sample 5a. A second set of samples was prepared by dispensing 3 ml of nitrogen into the syringes containing the uniform paste. The syringes were capped without further mixing and then stored at 4° C. The samples were designated as samples 5b. The third set of samples were prepared by extruding the paste back and forth between the first syringe and a second syringe containing 3 ml of nitrogen until all of the nitrogen was homogenously incorporated into the paste. The fill-volume of the resulting homogeneous compositions was approximately 9 ml and the density of the composition was approximately 0.7 grams/ml. The syringes were then capped and some of the pre-filled syringes were sterilized by irradiation at a dose of 25 kGy. The Peak Expression Force of the three sets of samples was determined and presented in Table 2.

TABLE 2

| Samples | Peak Expression Force pounds (n = 5) |
|---|---|
| Sample 5a | 21.7 |
| Sample 5b | 20.7 |
| Sample 5c | 15.5 |

As the data in Table 2 indicates, homogeneous distribution/dispersion of the gas throughout the paste is essential to reduce the peak expression force of the composition prior to irradiation and to maintain the lower peak expression force of the composition after irradiation, compared to pastes containing no gas or having gas poorly or partially dispersed there through.

Example 6

One gram of Surgifoam® gelatin powder was mixed with 5 ml of normal saline to form a uniform paste. The resulting paste was back-loaded into a 10 cc BD luer syringe. All air was extruded from the syringe leaving the paste packed in the syringe. A second set of 10 cc syringes containing nitrogen with volume ranging from 1 ml to 4 ml, respectively, was fitted to the first via a two-way luer connector. The paste was extruded into the gas and then passed back and forth between the two syringes until all of the gas was homogeneously incorporated into the paste. The fill-volume of the resulting composition was approximately 6-10 ml and the density was approximately 0.60 to 1.0 grams/ml, each depending on the volume of gas introduced into the paste. The syringes were then capped and some of the pre-filled syringes were sterilized by irradiation at a dose of 25 kGy.

Sterilized samples were noted as samples 6a through 6e, respectively. The Peak Expression Force of the sterilized samples was determined and presented in Table 3.

TABLE 3

| Samples | Gas Volume (ml) | Density (g/ml) (Pre-sterilized) | Peak Expression Force pounds n = 5 |
|---|---|---|---|
| Sample 6a | 0 | 1.00 | 14.8 |
| Sample 6b | 1 | 0.86 | 12.9 |
| Sample 6c | 2 | 0.75 | 10.6 |
| Sample 6d | 3 | 0.66 | 8.6 |
| Sample 6e | 4 | 0.60 | 8.0 |

Example 7

One gram of Surgifoam gelatin powder was mixed with 5 ml of normal saline to form a uniform paste. The resulting paste was back-loaded into a 10 cc BD luer syringe. All air was extruded from the syringe, leaving the paste packed in the syringe. A second set of 10 cc syringes containing air with volume ranging from 0 ml to 4 ml, respectively, were fitted to the first syringe via a two-way luer connector. The paste was extruded into the gas and then passed back and forth between the two syringes until all of the gas was homogenously incorporated into the paste. The fill-volume of the resulting composition was approximately 6-10 ml and the density was approximately 0.60 to 1.0 grams/ml, each depending on the volume of gas introduced into the paste. The syringes were then capped and some of the filled syringes were sterilized by irradiation at a dose of 25 kGy. Sterilized samples were noted as samples 7a through 7e, respectively.

The Peak Expression Force of the sterilized samples was determined and presented in Table 4.

TABLE 4

| Samples | Gas Volume (ml) | Density (g/ml) (Pre-sterilized) | Peak Expression Force pounds n = 5 |
|---|---|---|---|
| Sample 7a | 0 | 1.00 | 14.8 |
| Sample 7b | 1 | 0.86 | 11.0 |
| Sample 7c | 2 | 0.75 | 10.9 |
| Sample 7d | 3 | 0.66 | 10.1 |
| Sample 7e | 4 | 0.60 | 10.0 |

Example 8

Hemostatic Performance of Different Materials in Porcine Splenic Biopsy Punch Model A porcine spleen biopsy punch model was used for evaluation of the hemostatic properties of samples prepared in Examples 1 through 7 and 9. A 6-mm biopsy punch was used to cut a tissue flap 3 mm deep. The tissue flap was cut out and 0.4 ml of the test materials was applied to the wound site. Manual compression was held over the wound site for 2 minutes. The wound site was then observed for up to 3 minutes for signs of bleeding. If bleeding was observed, additional applications of manual compression for 30 seconds each time were used until complete hemostasis was achieved. Table 5 lists the results of the evaluation. Results for unsterilized or sterilized samples are represented as an average values for all samples tested.

TABLE 5

| Samples | Number of Compressions | Time to Hemostasis (min:sec) |
|---|---|---|
| Samples 1a | 3 | 3:35 (n = 2) |
| Samples 2a | 3 | 3:33 (n = 2) |
| Samples 1b | 1 | 2:00 (n = 3) |
| Samples 2b | 2 | 3:00 (n = 6) |

Example 9

Two vials of lyophilized Bovine thrombin (20,000 units Thrombogen JJMI) were reconstituted in 20 ml of saline to provide a working solution of 1000 u/ml. Clotting activity was measured in an in vitro test as described in Example 10. One vial of this material was stored at 4-8° C. and the clotting activity measured at day 1, day 8 and day 30, respectively. The second vial was sterilized by gamma irradiation (25 kGy) and the clotting activity measured as above. The unsterilized and sterilized samples were designated samples 9a and 9b, respectively. Both sterilized and unsterilized samples were stored at 4-8° C. between measurements.

Another 2 vials of 20,000 units of lyophilized bovine thrombin were reconstituted in saline containing 0.005% benzalkonium chloride and 5% glycerol. One vial was stored at. 4-8° C. and the clotting activity was measured at day 0, day 1, day 8 and day 30. The second vial was sterilized by gamma irradiation (25 kGy) and the clotting activity measured as above. In between measurements both the sterilized and unsterilized samples were stored at 4-8° C. The unsterilized and sterilized samples were designated samples 9c and 9d, respectively.

Several samples of gelatin paste containing the thrombin noted above were prepared by mixing 1 gram of Surgifoam gelatin powder with 5 ml of thrombin solution. The resulting paste was loaded into a 10 cc syringe. Samples were then either sterilized at 25 kGy followed by storage at 4-8° C., or stored unsterilized at 4-8° C. Samples so prepared are designated and identified below.

Sample 9e=1 g Surgifoam® powder plus 5 ml of sample 9a; Sterilized

Sample 9f=1 g Surgifoam® powder plus 5 ml of sample 9a plus 3 ml Nitrogen: Foamed and Sterilized Sample 9g=1 g Surgifoam® powder plus 5 ml of sample 9c; Unsterilized Sample 9h=1 g Surgifoam® powder plus 5 ml of sample 9c; Sterilized Sample 9i=1 g Surgifoam® powder plus 5 ml of sample 9c plus 3 ml Nitrogen; Foamed and Sterilized

Example 10

Measurement of Thrombin Activity by an In Vitro Coagulation Test in a Fibrometer Instrument (BBL)

Serial dilutions of test sample containing thrombin were prepared in Veronal buffer pH 7.2. 0.2 ml of pooled normal plasma (Citrol Level 1 control plasma-Dade Diagnostics) was warmed to 37° C. in the fibrometer incubator block. 0.1 ml of pre-warmed sample dilution was added to the plasma and the timer started simultaneously. The time to clot formation was recorded. All samples were tested in duplicate and an average clotting time calculated. Data was graphed as the $\log_{10}$ dilution vs. $\log_{10}$ clotting time and a regression analysis performed. Freshly prepared thrombin was considered to have 100% activity and all other samples were calculated as a percentage of the activity relative to the freshly prepared thrombin. Results are presented in Table 6 and Table 7.

TABLE 6

Effect of Storage time on Thrombin Activity:
Stabilization by Formulated Gelatin Paste

| Storage Solution | Percent Loss in Thrombin Activity | | | |
|---|---|---|---|---|
| (Stored at 6° C.) | Time 0 | Day 1 | Day 8 | Day 30 |
| 9a | 0 | 0 | 53.3 | 90.8 |
| 9c | 0 | NA | 41.1 | 82.9 |
| 9g | 0 | 0 | 0.8 | 0 |

TABLE 7

Effect of Gamma Irradiation on Thrombin Activity:
Stabilization by Formulated Gelatin paste

| Media for Sterilized Thrombin * Samples (5 ml/g gelatin | % Loss in Thrombin Activity | |
|---|---|---|
| powder-25 kGy Dose) | Day 6 | Day 20 |
| 9b | 100 | 100 |
| 9d | 96.0 | 100 |
| 9e | 72.6 | NA |
| 9f | 66.8 | 56-72 |
| 9h | 79.2 | ND |
| 9i | 63.8 | 61-73 |

TABLE 8

In vivo Hemostasis Performance of
Pre-filled Thrombin/Gelatin Paste

| TIME: Sample | Number of Compressions | Time to Hemostasis (min:sec) |
|---|---|---|
| Day 0: 9g | 1 | 0:30 |
| Day 42: 9g | 1 | 0:30 |
| Day 42: 9g | 1 | 0:30 |
| Day 42: 9h | 1 | 0:30 |
| Day 42: 9h | 1 | 0:30 |

Example 11

One liter of a saline solution containing 0.005% by weight of benzalkonium chloride and 5% weight of glycerol were poured into a mixing vessel (Ross Mixer, Model DPM2, Serial #75308) and the mixer blades engaged in an operating mode. Nitrogen gas was introduced into the solution via a tube connected to a nitrogen source in a continuous bubbling manner. The mixture of solution and gas was stirred at 70 Hz for approximately 10 minutes in order to form a foam as described herein above. The addition of the solid particles was commenced after formation of the foam using an addition-funnel attached to the entry port of the mixing vessel. 200 grams of gelatin powder were added over a time period of about 3 minutes. The mixing was continued for about 15 minutes after total powder addition at 70 Hz, followed by additional mixing for about 2 minutes at a reduced blade speed of about 12 Hz. Upon completion of the mixing, the density of the composition in the mixing vessel was measured using the solvent method as described above to ensure that the density was within acceptable parameters, indicating a substantially homogenous dispersion of the particles in the foam.

The composition was transferred to the desired level in the holding vessel of the filling apparatus equipped with an auger having 7 flights. The distance between the flights at the upper portion of the screw was about 3.75 cm, while the distance between the flights at the lower portion of the screw was about 1.5 cm. The composition then was dispensed into syringes by way of the auger screw. Approximately 6 milliliters (ml) of composition was placed in each syringe. The filling was performed using the syringe filling apparatus at a rate of approximately 36 ml/minute to about 72 ml/minute. The holding vessel was replenished with fresh flowable hemostatic composition as the level gradually decreased. Upon completion of the filling procedure, the density of the flowable hemostatic composition in the syringe was measured as described above. Results are reported in Table 9.

Example 12

Two liter of a saline solution containing 0.005% by weight of benzalkonium chloride and 5% weight of glycerol were poured into a mixing vessel (Ross Mixer, Model DPM2, Serial #75308) and the mixer blades engaged in an operating mode. Nitrogen gas was introduced into the solution via a tube connected to a nitrogen source in a continuous bubbling manner. The mixture of solution and gas was stirred at 70 Hz for approximately 10 minutes in order to form a foam as described herein above. The addition of the solid particles was commenced after formation of the foam using an addition-funnel attached to the entry port of the mixing vessel. 400 grams of gelatin powder were added over a time period of about 5 minutes. The mixing was continued for about 10 minutes after total powder addition at 70 Hz, followed by additional mixing for about 2 minutes at a reduced blade speed of about 12 Hz. Upon completion of the mixing, the density of the composition in the mixing vessel was measured using the solvent method as described above to ensure that the density was within acceptable parameters, indicating a substantially homogenous dispersion of the particles in the foam.

The composition was transferred to the desired level in the holding vessel of the filling apparatus equipped with an auger having 7 flights. The distance between the flights at the upper portion of the screw was about 3.75 cm, while the distance between the flights at the lower portion of the screw was about 1.5 cm. The composition then was dispensed by way of the auger screw. Approximately 6 milliliters (ml) of composition was dispensed into each syringe at a rate of approximately 120 ml/minute. The holding vessel was replenished with fresh flowable hemostatic composition as the level gradually decreased. Upon completion of the filling procedure, the density of the flowable hemostatic composition in the syringe was measured as described above. Results are reported in Table 9.

TABLE 9

Effect of filling rate on the density of paste

| Syringe Number | Density of Paste (gm/ml) Rate of filling | | | | |
|---|---|---|---|---|---|
| | 12 ml/min | 18 ml/min | 36 ml/min | 72 ml/min | 120 ml/min |
| 1 | <0.659 | <0.626 | <0.626 | <0.626 | <0.626 |
| 10 | <0.695 | <0.626 | <0.626 | <0.626 | <0.626 |
| 15 | <0.703 | <0.703 | <0.626 | <0.626 | |
| 20 | <0.703 | <0.703 | <0.626 | <0.626 | |
| 25 | <0.703 | <0.703 | <0.626 | <0.626 | |
| 30 | <0.718 | <0.703 | <0.659 | <0.626 | |
| 35 | <0.745 | <0.718 | <0.659 | <0.626 | |
| 40 | NA | <0.718 | <0.659 | <0.626 | |
| 50 | NA | NA | <0.659 | <0.626 | <0.626 |
| 60 | NA | NA | <0.703 | <0.659 | |
| 80 | NA | NA | <0.703 | <0.659 | |
| 100 | NA | NA | NA | <0.703 | <0.626 |
| 120 | NA | NA | NA | <0.703 | |
| 140 | NA | NA | NA | <0.703 | |
| 150 | NA | NA | NA | <0.703 | <0.626 |
| 600 | NA | NA | NA | NA | <0.626 |

*: Density of paste measured as extruded out of the Auger. Each exudate is approximately 6 ml in volume.

Table 9 demonstrates the effect that the rate of filling may have on the resulting density of the paste. It first is noted that for a particular rate of filling, i.e. number of syringes filled per minute, the density of the composition indicated to be less than a particular value for the particular number of syringe is greater than the density value measured at the previous number of syringe. For example, at 12 ml/minute, the density of the composition in the 25$^{th}$ filled syringe is less than 0.703 but greater than 0.659. It is noted that at higher filling rates, the consistency of the composition may be maintained within acceptable parameters over longer periods of time. As noted, at a higher filling rate, e.g. 72 ml/minute, the density of the composition is maintained to be no greater than 0.703 g/ml at the 150$^{th}$ syringe filled, while at a filling rate of 12 ml/minute, the same relative change in the density of the composition is noted at the 25$^{th}$ syringe filled. It is noted that the particular rates of filling noted herein are applicable to the particular apparatus and compositions disclosed herein and may in fact vary depending on apparatus design and composition.

We claim:

1. A medical device comprising:
   a substantially homogeneous hemostatic composition comprising:
      a continuous, biocompatible liquid phase;
      a solid phase comprising particles of a biocompatible polymer suitable for use in hemostasis and which is substantially insoluble in said liquid phase; and
      a discontinuous gaseous phase comprising a biocompatible gas, said continuous liquid phase comprising said solid phase and said discontinuous gaseous phase substantially homogenously dispersed there through, wherein the ratio of said liquid phase, said solid phase and said gaseous phase is effective to provide said composition with hemostatic properties,
      wherein said gas is selected from the group consisting of nitrogen, carbon dioxide, xenon and argon; and
   a device having disposed therein said substantially homogeneous hemostatic composition, and configured to apply said substantially homogeneous hemostatic composition to a site requiring hemostasis.

2. The medical device of claim 1 wherein said liquid phase comprises saline.

3. The medical device of claim 1 wherein said biocompatible polymer is selected from the group consisting of proteins and polysaccharides.

4. The medical device of claim 3 wherein said protein is selected from the group consisting of gelatin, collagen, fibrinogen and fibronectin.

5. The medical device of claim 4 wherein said protein comprises gelatin.

6. The medical device of claim 1 wherein the average diameter of said particle is from about 40 to about 1200 microns.

7. The medical device of claim 1 wherein said particles, said continuous liquid phase and said gaseous phase are present in said substantially homogeneous hemostatic composition at a ratio of from about 1:2:1 to about 1:12:13, based on g:ml:ml.

8. The medical device of claim 1 wherein the density of said substantially homogeneous hemostatic composition is from about 0.9 g/mil to about 0.3 g/ml.

9. The medical device of claim 1 wherein said composition further comprises a functionally effective amount of an additive selected from the group consisting of antimicrobial agents, foaming agents, foam stabilizers, surfactants, antioxidants, humectants, thickeners, lubricants, diluents, wetting agents, irradiation stabilizers, plasticizers, heparin neutralizers, procoagulants and hemostatic agents.

10. The medical device of claim 1 wherein said composition comprises up to about 20 weight percent of glycerol, based on the weight of said liquid phase.

11. The medical device of claim 1 wherein said composition comprises up to about 1 weight percent of a quaternary amine, based on the weight of said liquid phase.

12. The medical device of claim 1 wherein said composition and said device are sterile.

13. The medical device of claim 9 wherein said functional additive is selected from the group consisting of fibrinogen and thrombin.

14. A medical device comprising:
   a flowable hemostatic composition comprising:
      a continuous, biocompatible liquid phase;
      a solid phase comprising particles of a biocompatible polymer suitable for use in hemostasis and which is substantially insoluble in said liquid phase; and
      a discontinuous gaseous phase comprising a biocompatible gas, said solid phase and said discontinuous gaseous phase are uniformly dispersed throughout the continuous liquid phase such that a ratio of solid:liquid:gas and the density of any portion or cross-section of the composition is substantially the same,
      wherein said composition is in a form of a foam such that the discontinuous gaseous phase is dispersed within the continuous liquid phase; and
      wherein said gas is selected from the group consisting of nitrogen, carbon dioxide, xenon and argon; and
   a device having disposed therein said composition, and configured to apply said composition to a site requiring hemostasis.

15. The medical device of claim 14 wherein said ratio is from about 1:4:1 to about 1:8:9, based on g:ml:ml; and said density of said composition is from about 0.8 g/ml to about 0.6 g/ml.

* * * * *